United States Patent
Garbasch et al.

(12) 
(10) Patent No.: US 6,234,356 B1
(45) Date of Patent: May 22, 2001

(54) APPLICATOR AND ELECTRO-MECHANICAL APPLICATOR DRIVE SYSTEM

(75) Inventors: Allan Garbasch, Hillerød; Niels Hvid, Vedbaek, both of (DK); David Cianciolo, Largo, FL (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/643,704

(22) Filed: Aug. 22, 2000

Related U.S. Application Data
(60) Provisional application No. 60/150,570, filed on Aug. 25, 1999.

(51) Int. Cl.$^7$ .................................................. A61M 31/00
(52) U.S. Cl. ...................... 222/137; 222/137; 222/327; 222/386; 604/82
(58) Field of Search ............................. 222/63, 135, 136, 222/137, 326, 327, 386; 604/82, 83

(56) References Cited

U.S. PATENT DOCUMENTS

| | | | |
|---|---|---|---|
| 4,228,924 | * 10/1980 | Gilbert | ........................... 222/137 X |
| 4,631,055 | * 12/1986 | Redl et al. | ...................... 222/135 X |
| 4,846,405 | * 7/1989 | Zimmerman | ....................... 604/83 X |
| 5,226,877 | * 7/1993 | Epstein | ............................... 604/82 X |
| 5,368,653 | * 11/1994 | Lonneman et al. | ..................... 604/82 |
| 5,605,541 | * 2/1997 | Holm | .................................... 604/82 |
| 5,759,169 | * 6/1998 | Marx | .................................... 604/82 |
| 5,975,367 | * 11/1999 | Coelho et al. | ........................ 222/137 |
| 6,165,201 | * 12/2000 | Sawhney et al. | .................. 604/82 X |

FOREIGN PATENT DOCUMENTS

WO 97/20585 * 6/1997 (WO) .
WO 98/20931 * 5/1998 (WO) .

* cited by examiner

Primary Examiner—Kenneth Bomberg
(74) Attorney, Agent, or Firm—Theodore R. Furman, Jr.; Stuart E. Krieger

(57) ABSTRACT

An applicator and an electro-mechanical applicator drive system for automatically emptying the liquid components from respective syringes in a controlled manner for co-applying fibrin sealant components with a gas to form a spray. The applicator drive system includes a piston elevator section which moves the syringe pistons of the respective syringes in unison. The applicator drive system further includes at least one syringe piston force sensor which senses a force required by the piston elevator section to move at least one of the syringe pistons forward and outputs a force sensor signal. A controller is provided which controls movement of a piston elevator of the piston elevator section based on the force sensor signal.

22 Claims, 12 Drawing Sheets

APPLICATOR AND ELECTRO-MECHANICAL APPLICATOR DRIVE SYSTEM

This application claim benefit to Provisional Application 60/150,570 filed Aug. 25, 1999.

BACKGROUND OF THE INVENTION

1. Field of the Invention

The present invention generally relates to an applicator system for co-applying two or more liquid components from separate containers via separate liquid channels or tubes having separate outlets and, more particularly, to an electro-mechanical applicator drive system for automatically emptying the liquid components from respective syringes in a controlled manner for co-applying fibrin sealant components with a gas to form a spray.

2. Description of the Related Art

Devices and methods for the enhanced application of two or more liquids for forming a biopolymer, e.g., a surgical sealant, are disclosed in WO 97/20585 and WO 98/20931 both of which are commonly owned by Bristol-Myers Squibb Company and both of which are incorporated herein by reference. These two international publications disclose a device and methods which provide uniform mixing at low air and liquid flow rates in order to apply thin, even coats of sealant with reduced waste and aerosols. Examples of suitable applications for the device and methods are fibrin sealants wherein a gas, such as air, is used to help mix and apply two or more liquid components which could be a fibrinogen solution and a thrombin solution or a fibrin monomer solution and a fibrin-polymerizing solution, e.g., pH 10 buffer, as set forth in European Patent 592,242 to Edwardson et al.

The present invention focuses on the applicator drive system and is suitable for incorporation into an application system as described in WO 97/20585 and also WO 98/20931. As shown in FIG. 1, an application system or applicator is generally designated with the reference numeral 10 including an applicator spray pen 11 having an optional handle 12 and a spray tip or nozzle 14 and a spray pen actuator button 16 to initiate application. The spray nozzle or tip 14 terminates in a generally flat lip surface 14' which is substantially normal to the longitudinal direction of the tip 14 and which includes exit apertures (not shown) through which gases and liquids are dispensed during application. The applicator spray pen 11 is in fluid communication via tubing or tubing system (18, 30, 32, 34, 36) with a dispenser 20 of liquids and gases to be applied.

The component source containers preferably are in the form of syringes (60, 61) wherein the pistons in the syringe cartridges can be actuated to supply the gas and liquid components to the spray nozzle 14 of the applicator spray pen 11. The present invention is primarily concerned with the applicator drive system for simultaneously actuating the pistons of the syringes to provide an accurate and constant volume flow from the spray nozzle 14 of the applicator spray pen 11.

SUMMARY OF THE INVENTION

It is an object of the present invention to provide an applicator and an electro-mechanical applicator drive system for automatically emptying the liquid components from respective syringes in a controlled manner for co-applying fibrin sealant components with a gas to form a spray. The electro-mechanical applicator drive system is a non-sterile device which preferably houses fibrin 1 and pH 10 buffer syringe cartridges and feeds these solutions to a hand-held applicator spray pen via a tubing system such as a multilumen catheter.

More specifically, the present invention relates to an electro-mechanical applicator drive system for automatically emptying liquid components from a plurality of syringes, each of the syringes having a corresponding syringe piston, the applicator drive system comprising: a piston elevator section which moves the syringe pistons in unison; at least one syringe piston force sensor which senses a force required by the piston elevator section to move at least one of the syringe pistons forward and outputs a force sensor signal; and a controller which controls movement of the piston elevator section based on the force sensor signal.

The piston elevator section comprises: a support bar having a cross plate mounted thereto; a linear slide fixedly mounted to the support bar; a linear slide block slidably mounted for up and down movement on the linear slide; a piston elevator fixedly mounted to the linear slide block, the syringe pistons being mounted to the piston elevator; a piston actuator flag fixedly mounted to the piston elevator; and a piston stepper motor fixedly mounted to the cross plate and having an axially movable motor shaft extending downwardly and having a lower end connected to the piston actuator flag. Thus, as the motor shaft moves axially up or down, the piston actuator flag, the linear slide block, the piston elevator and the syringe pistons all move up or down as a unit with respect to the linear slide.

The applicator drive system may further include a syringe elevator section which moves the syringes for loading/removal. The syringe elevator section comprises: the support bar having the cross plate mounted thereto; the linear slide fixedly mounted to the support bar; a monorail plate slidably mounted for up and down movement on the linear slide; a syringe actuator flag fixedly mounted to the monorail plate; a syringe elevator fixedly mounted to the monorail plate; a syringe stepper motor fixedly mounted to the cross plate and having an axially movable motor shaft extending upwardly and having an upper end connected to the syringe actuator flag. Thus, as the motor shaft moves axially up or down, the syringe actuator flag, the monorail plate, and the syringe elevator all move up or down as a unit with respect to the linear slide.

The invention further provides an application system for co-applying a plurality of liquid components from a plurality of corresponding syringes, each of the syringes having a corresponding syringe piston. The application system comprises: a) a standalone housing unit; a dispenser disposed within the standalone housing unit and having an applicator drive system; and c) a disposable application set which includes a connector to which the syringes are installed and which is operative to be loaded into the dispenser, a hand-held applicator, and a tubing system for providing fluid communication between the connector and the hand-held applicator. The applicator drive system comprises: i) a piston elevator section which moves the syringe pistons in unison; ii) at least one syringe piston force sensor which senses a force required by the piston elevator section to move at least one of the syringe pistons forward and outputs a force sensor signal; and iii) a controller which controls movement of the piston elevator section based on the force sensor signal.

BRIEF DESCRIPTION OF THE DRAWINGS

Other features and advantages of the present invention will be apparent from the following description taken in connection with the accompanying drawings, wherein.

DETAILED DESCRIPTION OF THE PREFERRED EMBODIMENTS

Figure 1:
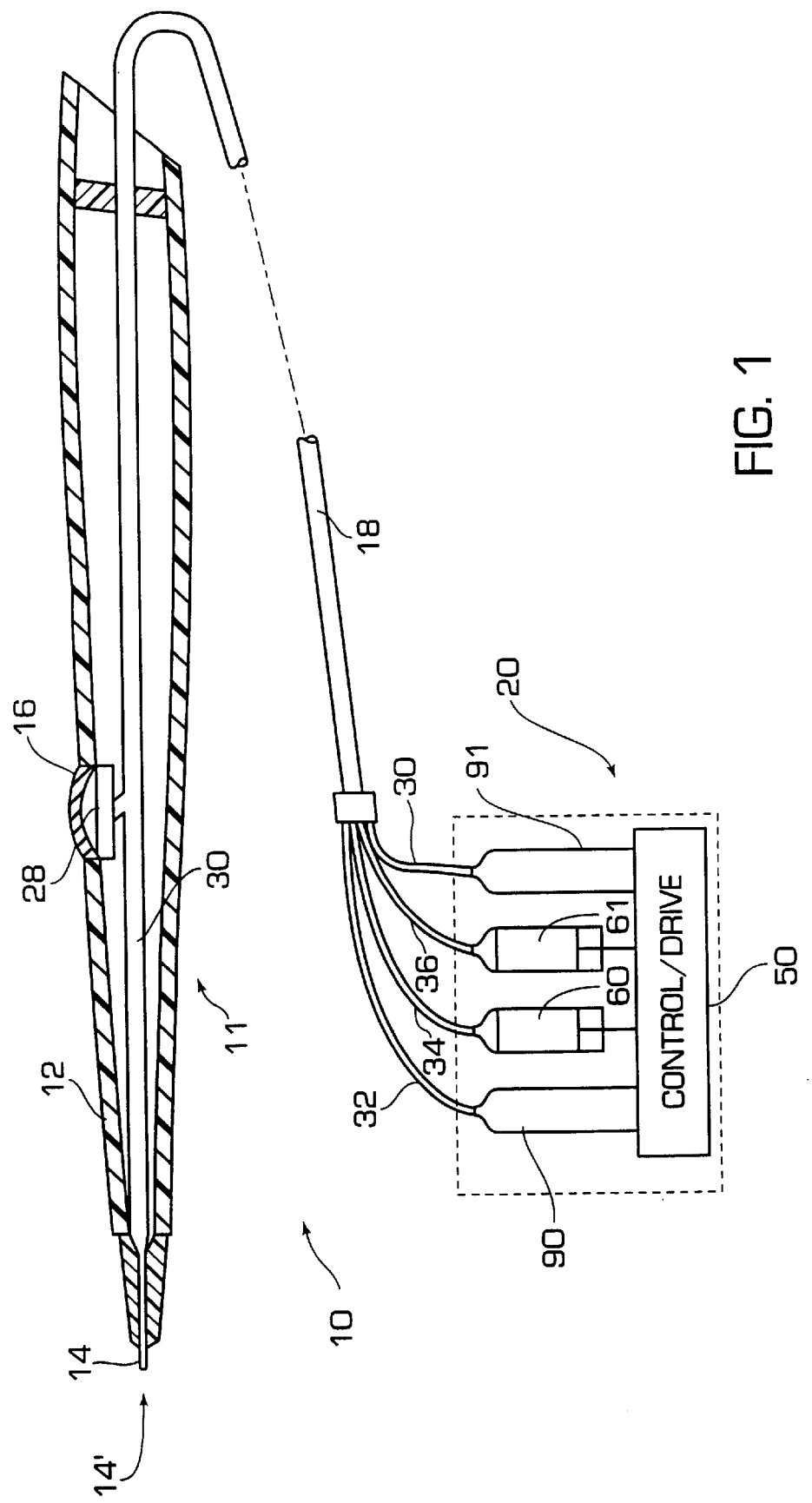
FIG. 1 is a lateral view of the overall application system in which the applicator drive system of the present invention may be incorporated.
Figure 2:
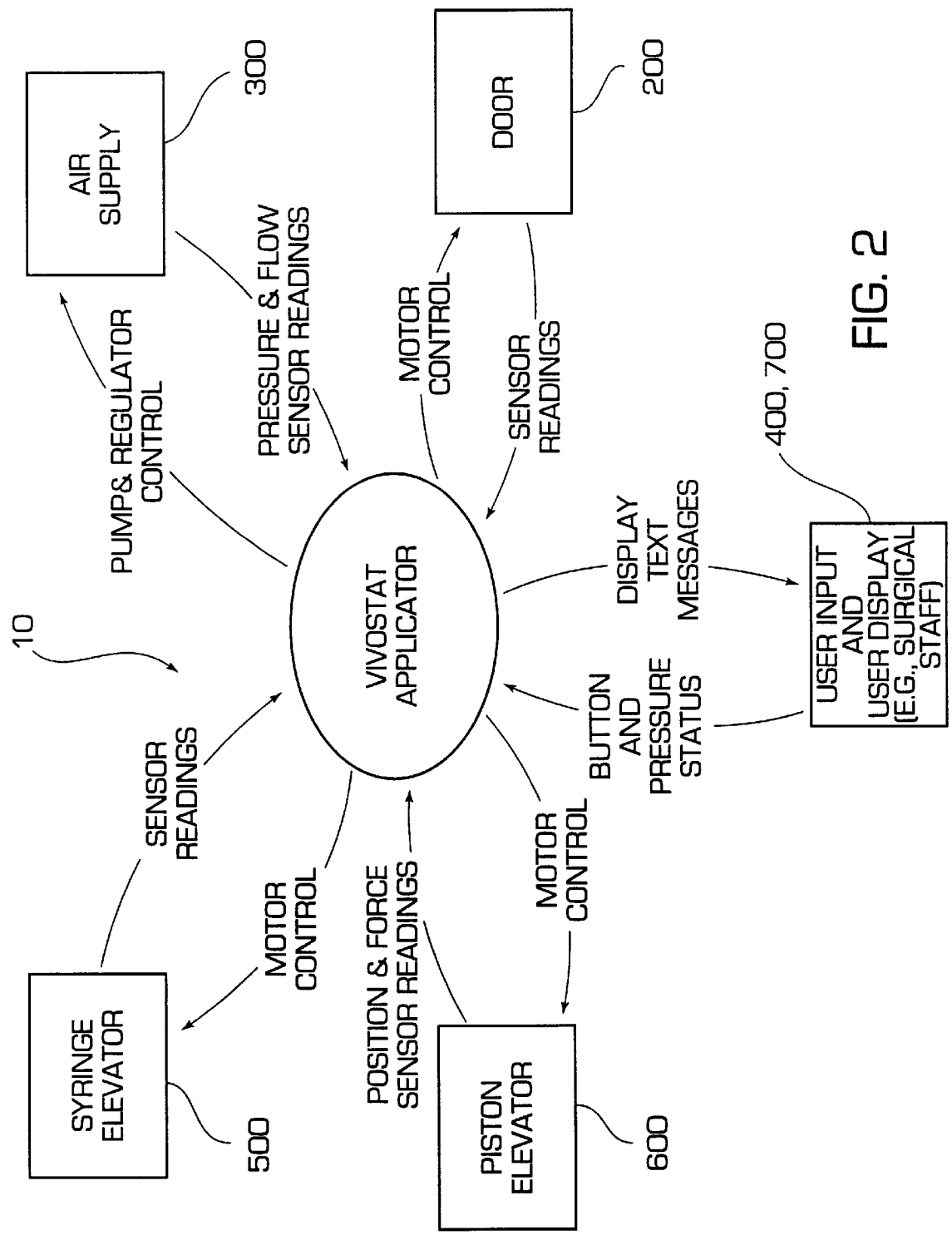
FIG. 2 is a context diagram of the applicator according to the present invention.
Figure 3:
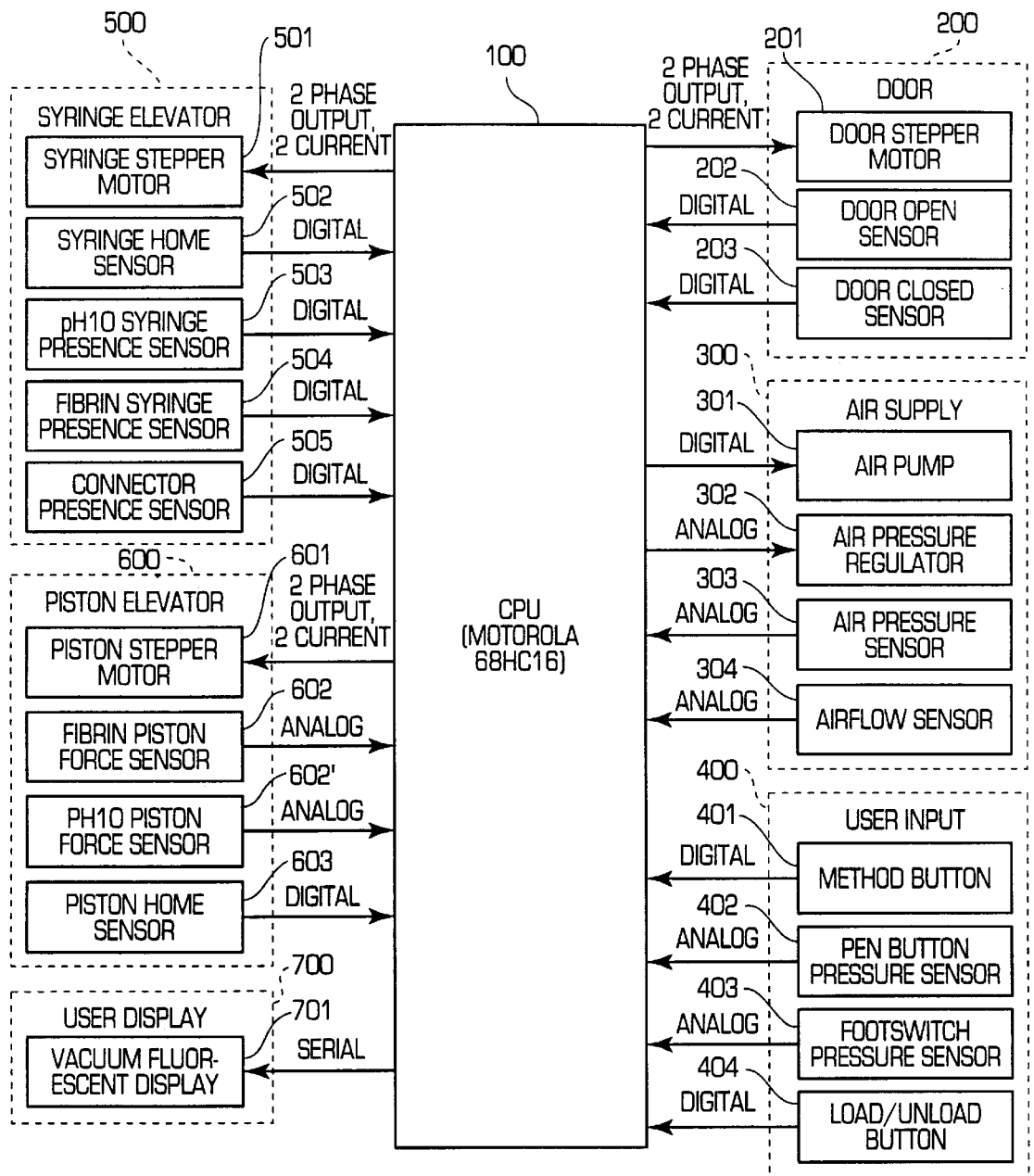
FIG. 3 is a block diagram of the applicator according to the present invention.
Figure 4:
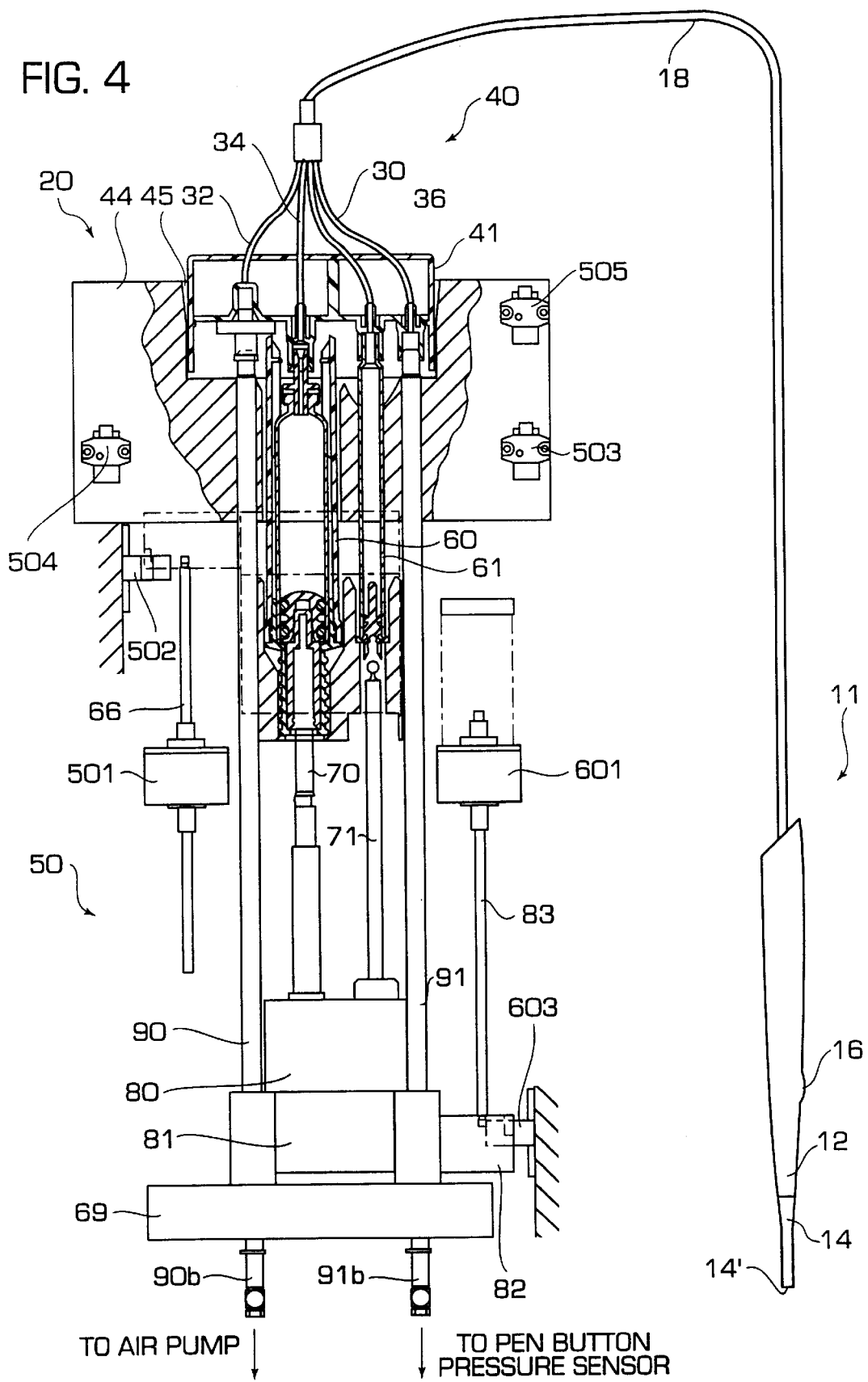
FIG. 4 is a schematic, rear elevational view in partial cross section of the dispenser portion according to the present invention.
Figure 5:
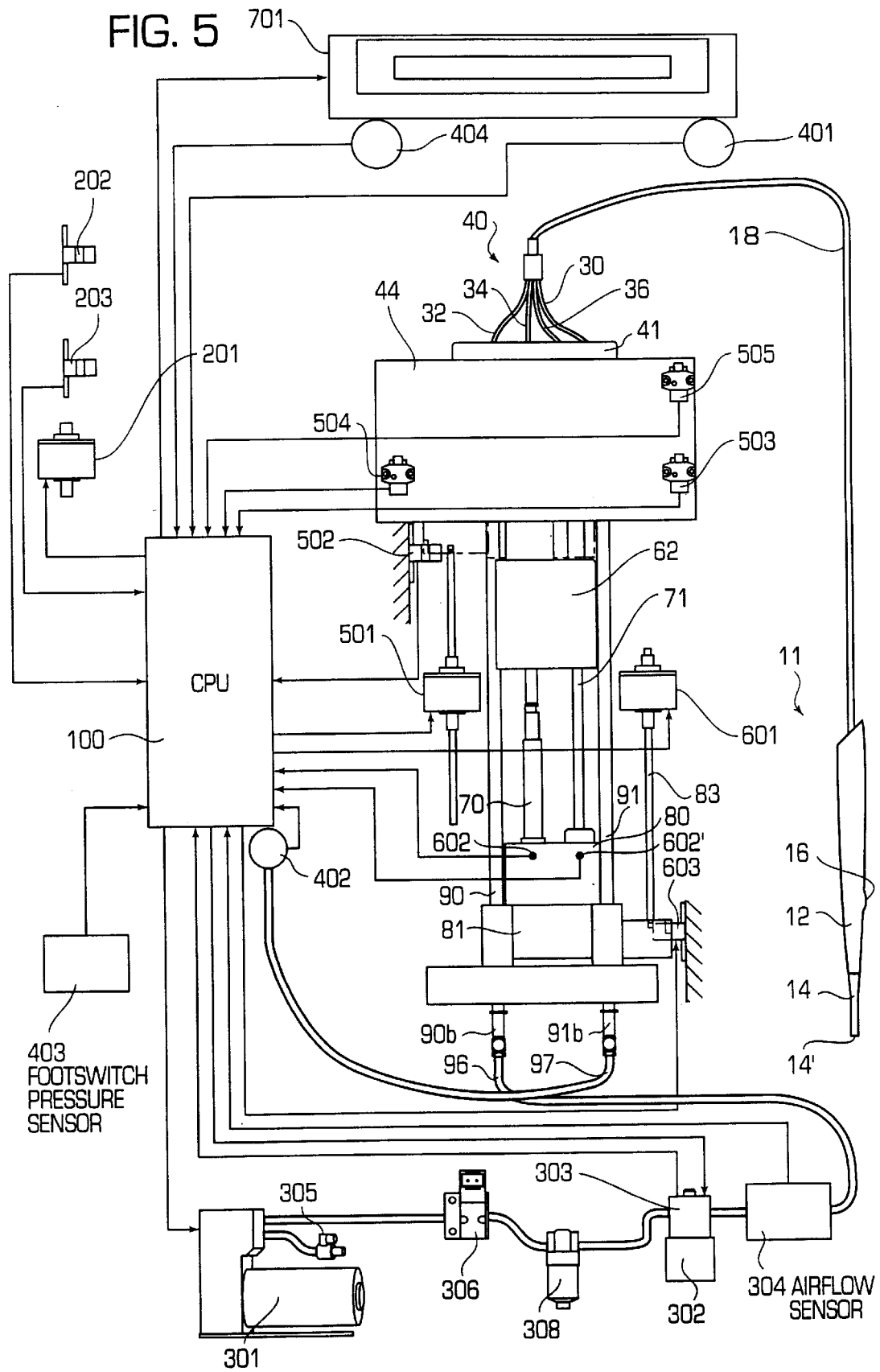
FIG. 5 is a schematic view of the applicator according to the present invention and which more fully develops the block diagram of the applicator as shown in FIG. 3.

The present invention will now be described with reference to the drawings. As shown in FIGS. 1, 2 and 5, in general, the applicator 10, also referred to as the VIVOSTAT™ applicator, is a machine used for delivering a fibrin, pH 10, and an air mixture in the form of a sealant through a hand-held applicator spray pen 11 having a spray tip or nozzle 14. As shown in FIG. 4, a syringe 60 of fibrin, a syringe 61 of the pH 10 and a disposable assembly or application set 40 including a connector 41 and the applicator spray pen 11 are loaded into the VIVOSTAT™ applicator, which is a standalone cabinet or housing unit S which may be equipped with castors C for convenient relocation. (See FIGS. 9 and 10). When the operator presses either the spray pen actuator button 16, or a foot switch 403 (see FIGS. 3 and 5), the applicator drive unit automatically raises the syringe pistons 70, 71 to send streams of each solution in a predetermined proportion to the nozzle 14. The applicator 10 also controls a gas supply, such as air, that sends a stream of gas to the nozzle 14. At the spray tip or nozzle 14, the solutions are mixed with the air for co-applying the sealant components with the gas to form a spray.

The present invention is primarily concerned with the electro-mechanical applicator drive system 50 of the dispenser 20 and its interaction with the disposable application set 40, the fibrin syringe 60 and the buffer syringe 61.

A controller or control processor unit (CPU) 100, such as a Motorola 68HC16, controls the applicator 10 process and reports the status of the process. FIG. 2 is a context diagram of the VIVOSTAT™ applicator 10. As shown in FIGS. 3 and 5, the CPU 100 is connected to various sensors and controllable devices in order to perform the various functions.

More specifically, with reference to FIGS. 2, 3 and 5, the CPU 100 is connected to a door stepper motor 201, a door open sensor 202 and a door closed sensor 203, for controlling the opening and closing of the access door 200 of the VIVOSTAT™ applicator 10.

The air supply section 300 for supplying air to the nozzle 14 in order to form a spray, includes an air pump 301, an air pressure regulator 302, an air pressure sensor 303, and an air flow sensor 304 all electrically connected to the CPU 100.

The VIVOSTAT™ applicator 10 further includes a user input section 400 which includes a method button 401, used to select different spraying methods, a pen button pressure sensor 402, a foot switch pressure sensor 403, and a load/unload button 404, all of which are electrically connected to the CPU 100.

The VIVOSTAT™ applicator 10 still further includes a syringe elevator section 500 which includes a syringe stepper motor 501, a syringe home sensor 502, a pH 10 syringe presence sensor 503, a fibrin syringe presence sensor 504, and a connector presence sensor 505. The applicator 10 also includes a piston elevator section 600 which includes a piston stepper motor 601, a fibrin piston force sensor 602, a pH 10 piston force sensor 602', and a piston home sensor 603.

Finally, the applicator 10 includes a user display section 700 which comprises a vacuum fluorescent display 701.

Each one of the above-described sections 200, 300, 400, 500, 600 and 700 will be discussed in more detail below with respect to the VIVOSTAT™ applicator 10 in connection with the drawing figures.

With reference to FIGS. 2–8, the syringe elevator section 500 is a motor driven assembly that moves the syringes within the applicator 10. Each syringe is a disposable cylindrical container for storing and dispensing liquids. The applicator 10 preferably, but not necessarily, contains two syringes, e.g., the fibrin syringe 60 and the pH 10 syringe 61. The primary purpose of the syringe elevator section 500 is to raise both of the syringes 60, 61 for easy loading/removal by the operator and for tightening the seal between the syringes and the connector 41. The connector 41 is a portion of the disposable assembly 40 which connects with the syringes 60, 61 and the air supply 300. The disposable assembly 40 comprises the tubing system 18, the nozzle tip 14, the spray pen 11, the pen button 16 and the connector 41.

Figure 6:
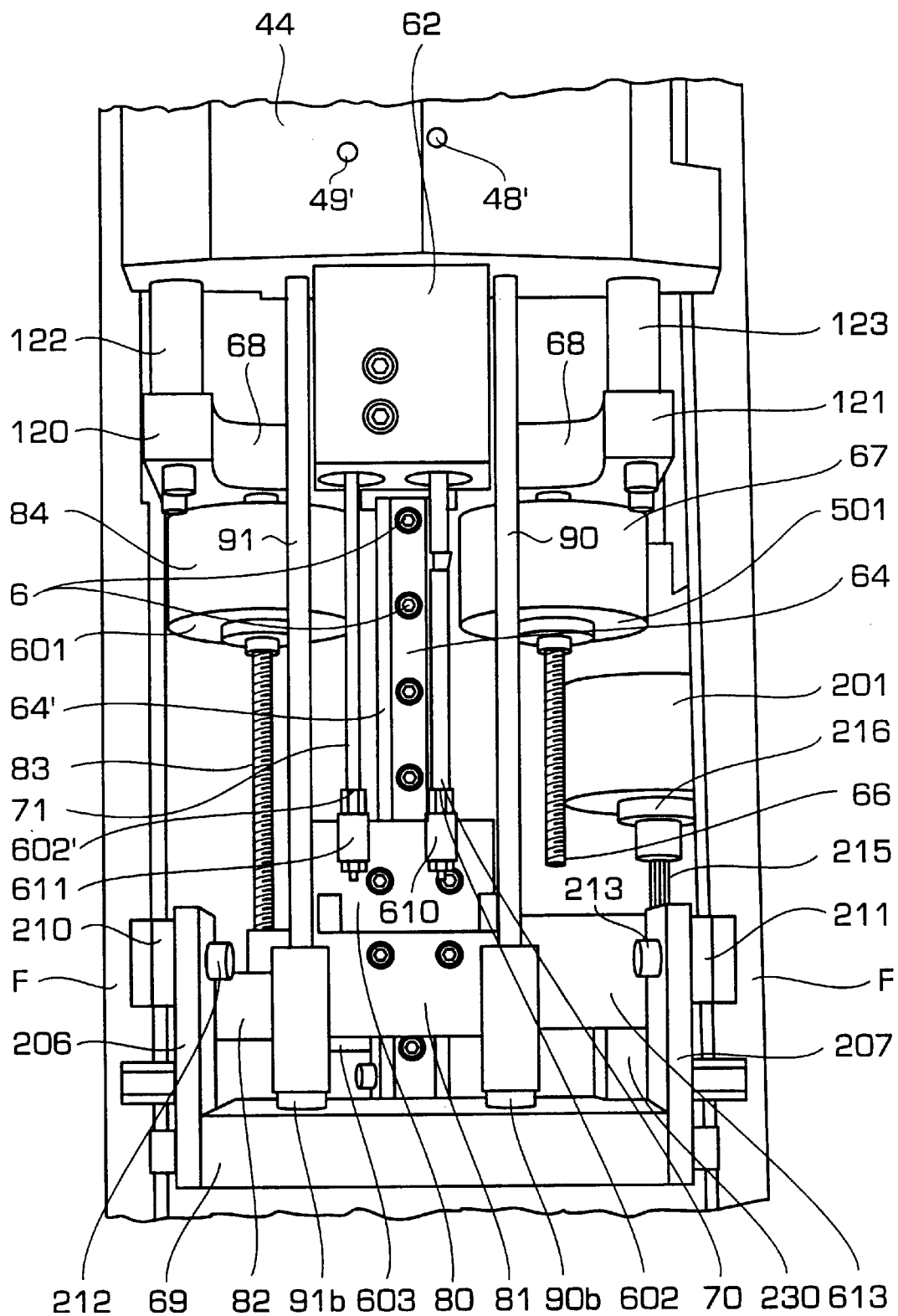
FIG. 6 is a fragmentary, frontal perspective view of the dispenser portion according to the present invention.

As best shown in FIG. 6, which is a front view such that the pH 10 syringe piston 71 and the fibrin syringe piston 70 are reversed from the position shown in the rear views of FIGS. 4 and 5, a syringe elevator or house 62 is mounted onto a monorail plate 63 (see FIG. 7) which is in turn slidably mounted onto a linear slide 64 so as to permit up and down movement of the syringe elevator 62. The linear slide 64 is fixedly attached by fasteners 6 to a vertical support bar 64'. The monorail plate 63 is connected to a syringe actuator flag 65. The syringe actuator flag 65 is in turn connected to the upper end of motor shaft 66 of the syringe stepper motor 501. The connection between the flag 65 and the shaft 66 is operative to permit some lateral movement of the shaft 66 to allow for mechanical slop.

The housing 67 of the syringe stepper motor 501 is fixedly mounted to a cross plate 68 which is in turn mounted to the vertical support bar 64'. The motor shaft 66 moves axially with respect to the housing 67 and through an opening in the cross plate 68 as the motor shaft 66 is driven axially by the syringe stepper motor 501. Thus, as the motor shaft 66 moves up or down, the syringe actuator flag 65, the monorail plate 63, and the syringe elevator 62 all move up or down as a unit with respect to the linear slide 64.

The vertical slide bar 64' is fixed to a base member 69 which in turn is pivotally mounted to a frame F, as will be discussed in detail below with respect to the door 200. The frame F is mounted within the standalone unit S (see FIG. 10).

The cross plate 68 has a pair of extension arms 120 and 121 which extend toward the front of the dispenser 20. Each extension arm 120, 121 has a cylindrical pillar 122, 123 vertically mounted thereon. A connector house 44 is fixedly mounted to the pillars 122, 123 so as to be positioned above the syringe elevator or house 62. The connector house 44 includes a recess 45 (see FIGS. 4 and 8) in the top surface thereof for receiving the disposable connector 41. The recess 45 preferably is oval-shaped so as to receive a complementary shaped connector 41. The connector house 44 has respective vertically extending syringe bores 46 and 47 for receiving the fibrin syringe 60 and the pH 10 syringe 61. Further, a pair of air tubes 90 and 91 are mounted to the base member 69 and extend vertically up through the bottom of the connector house 44 and have upper ends 90a and 91a protruding into the recess 45 of the connector house 44. The air tubes 90 and 91 are spring loaded such that they are biased upwardly into the recess 45 of the connector house 44. The lower ends 90b and 91b of the air tubes 90 and 91 extend through the base member 69 and are attached to respective hoses or flexible tubing 96 and 97, with the air tube 90 being connected to the air pump 301 and the air tube 91 being connected to the pen button pressure sensor 402.

Figure 8:
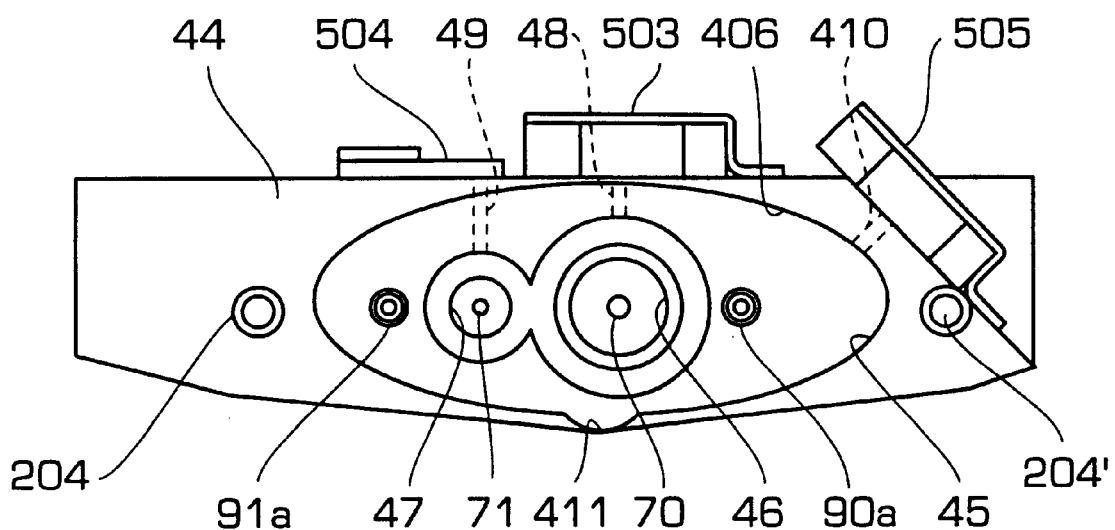
FIG. 8 is a top view of the connector house of the dispenser portion.

As shown in FIG. 8, within the recess 45 of the connector house 44, a small horizontal bore 410 is formed in a sidewall 406 thereof. The connector presence sensor 505 is mounted on the outside of the connector house 44 and is preferably in the form of an optical sensor which communicates with the horizontal bore 410 in order to sense the presence or absence of the connector 41 (see FIGS. 4 and 5). Moreover, each of the syringe bores 46 and 47 in the connector house 44 for receiving the fibrin and pH 10 syringes 60, 61 includes a small horizontal bore 48 and 49, respectively, with the fibrin syringe presence sensor 503 and the pH 10 presence sensor 504 being respectively mounted to a back portion of the connector house 44 and in registry with a corresponding bore 48, 49. The fibrin and pH 10 presence sensors are preferably optical sensors for sensing the presence or absence of the respective syringes. The front portion of the connector house 44 may include a pair of horizontal bores 48' and 49' (see FIG. 6) for facilitating cleaning of the lenses of the optical sensors 503 and 504. Moreover, the front portion of the recess 45 includes a channel 411 in the side wall 406 for proper alignment of the connector 41 in connector housing 44.

The syringe elevator 62 is movable between several positions by utilizing various interfaces as described in more detail below. The syringe elevator 62 positions include a home position, an engaged position, and a load position. The home position is the lowest position at which the syringe elevator 62 should ever be located. The home position is located using the syringe home sensor 502 (see FIGS. 4 and 5). The location of the home position is a prerequisite for all of the remaining syringe elevator section 500 operations. Moreover, the home position is the optimum position for the syringe elevator 62 when opening and closing a door member 205 (see FIG. 9) to the applicator 10. The engaged position is a position of the syringe elevator 62 above the home position and is the position in which the syringes 60, 61 are tightly locked together with the connector 41. The load position is the highest position at which the syringe elevator 62 should ever be located and is above the home position. In the load position, the fibrin syringe presence sensor 503 and the pH 10 syringe presence sensor 504 can sense the presence or absence of the syringes 60, 61 and connector presence sensor 505 can sense the presence or absence of the connector 41.

With reference to FIG. 5, the syringe stepper motor 501 is provided for raising, lowering and engaging the syringes with the connector 41. The syringe stepper motor 501 is preferably, but not necessarily, controlled by two stepper motor driver ICs driven by four bits of an output latch on the CPU 100, with two bits for the stepper motor phase, and two bits for the stepper motor current. Preferably, but not necessarily, the syringe stepper motor 501 is in the form of a non-captive shaft, linear actuator having a leadscrew as the motor shaft 66 which moves axially as it is driven by a threaded nut (not shown) which can be formed on the inside of the rotor disposed within the stepper motor housing 67. In order to generate linear motion, the leadscrew must be prevented from rotating. Thus, as the rotor (not shown) of the stepper motor turns, the internal threads thereon engage the leadscrew resulting in linear motion. Changing the direction of rotation of the stepper motor reverses the direction of linear motion. Of course, the rotary motion of the stepper motor can be converted into linear motion by other known mechanical means, such as but not limited to, rack and pinion, belt and pulley and other mechanical linkages. A suitable stepper motor is a 1.8 inch diameter stepper motor, 36000 Series, manufactured by Haydon Switch and Instrument (HSI) Inc., Waterbury, Conn.

The syringe home sensor 502 is an optical position sensor which is blocked when the syringe elevator 62 is at the home position. More specifically, the sensor 502 is fixedly mounted to a side of an upper end portion of the vertical support bar 64' at a location just above cross plate 68. A horizontally extending plate (not shown) projects from a side portion of the syringe actuator flag 65 and serves to block the light of the sensor 502 when the syringe elevator 62 is at the home position. On the other hand, the pH 10 syringe presence sensor 503 is, as noted above, an optical sensor connected to a digital input on the CPU 100, indicating the presence or absence of the pH 10 syringe 61. The fibrin syringe presence sensor 504 is, as noted above, an optical sensor connected to a digital input on the CPU 100, for indicating the presence or absence of the fibrin syringe 60. Finally, the connector presence sensor 505 is, as noted above, an optical sensor connected to a digital input of the CPU 100, for indicating the presence or absence of the connector 41 of the disposable assembly 40.

Accordingly, when the system is prompted by an operator, the syringe stepper motor 501 moves the syringe elevator 62 downwardly until the syringe actuator flag 65 reaches the syringe home sensor 502 (i.e., the home position). The syringe stepper motor 501 then stops the syringe elevator 62, and the connector 41 with the syringes 60, 61 installed thereon is loaded into the recess 45 of the connector house 44 and respective bores 46 and 47, and then the syringe stepper motor 501 moves the syringe elevator 62 upwardly to the engaged position such that the syringes 60, 61 are totally locked together with the connector 41. The syringe elevator remains engaged until the removal of the syringes 60, 61 is required after they have been emptied, at which time the syringe elevator 62 is moved downwardly to the home position. However, as noted above, before emptying the syringes 60, 61 utilizing the piston elevator section 600 as will be discussed in more detail below, the syringe elevator 62 is moved to the load position such that the fibrin syringe presence sensor 504 and the pH 10 presence sensor 503 can sense the presence or absence of the syringes 60, 61 and the connector presence sensor 505 can sense the presence or absence of the connector 41.

Referring to FIGS. 4, 5 and 6, the piston elevator section 600 is a motor driven assembly that moves the syringe pistons in unison within each syringe. Each syringe piston compresses the contents of the corresponding syringe. The syringe pistons, preferably but not necessarily a 1 ml piston 71 for the pH 10 and a 5 ml piston 70 for the fibrin, are first mounted onto the piston elevator 80. The piston elevator 80 is fixedly mounted on a linear slide block 81. The linear slide block 81 is slidably mounted for up and down movement on the linear slide 64. A piston actuator flag 82 is fixed to the piston elevator 80 and is in turn connected to the lower end of a motor shaft 83 of the piston stepper motor 601. The connection between the flag 82 and the shaft 83 likewise permits some lateral movement of the shaft 83 to allow for mechanical slop.

The housing 84 of the piston stepper motor 601 is fixedly mounted to the cross plate 68 on the other side of the linear slide 64 with respect to the syringe stepper motor 501. The motor shaft 83 preferably comprises a leadscrew which moves axially with respect to the housing 84 and through an opening in the cross plate 68 as the motor shaft 83 is driven axially by the piston stepper motor 601. Thus, as the motor shaft 83 moves axially up or down, the piston actuator flag 82, the linear slide block 81, the piston elevator 80 and the syringe pistons 70, 71 all move up or down as a unit with respect to the linear slide 64.

The syringe pistons 70, 71 are movable to several positions by utilizing several interfaces as discussed in detail below.

In particular, the home position is the lowest position at which the piston elevator 80 should ever be located. It is located by using the piston home sensor 603 which will described in more detail below. Locating the home position of the piston elevator 80 is a prerequisite for all the remaining piston elevator operations.

The disengaged position is the position where the piston elevator 80 has moved down far enough with respect to the connector house 44 to disengage the air tubes 90, 91 from the connector 41 so as to separate the connector 41 from the air supply 300 and the pen button pressure sensor 402. This position corresponds to the home position. On the other hand, the engaged position is the position where the piston elevator 80 has moved up far enough to release spring loaded air tubes 90, 91 such that the connector 41 can be engaged to the air supply 300 and the pen button pressure sensor 402. The engaged position is defined above the home position.

The primed position of the piston elevator 80 is the position where all the air has been flushed from the syringes 60, 61 and corresponding tubing 18. The primed position is determined by measuring the resistance of the fibrin syringe piston 70 using the fibrin piston force sensor 602 as the fibrin syringe piston 70 travels upwardly. As the fibrin enters the tubing 18, the resistance on the fibrin syringe piston 70 increases noticeably since the fibrin is much more viscous than air. Likewise, as the pH 10 enters the tubing 18, the resistance on the pH 10 syringe piston 71 increases noticeably since the pH 10 is more viscous than air. The pH 10 piston force sensor 602' measures the resistance of the pH 10 syringe piston 71 as it travels upwardly.

The empty position is the position whereby the piston elevator 80 has pushed the syringe pistons 70, 71 for the fibrin and the pH 10 as high as they will travel such that the respective syringes 60, 61 are emptied of their respective liquids. The empty position is defined above the home position.

The spraying range is the range of positions where upward movement of the syringe pistons 70, 71 will cause the respective liquids to be expelled through the spray nozzle 14. The spraying range starts at the primed position and extends up to the empty position.

The piston stepper motor 601, like the syringe stepper motor 501 is, preferably but not necessarily, a stepper motor controlled by two stepper motor driver ICs driven by four bits of an output latch on the CPU 100, with two bits for the stepper motor phase, and two bits for the stepper motor current. The piston stepper motor 601, like the syringe stepper motor 501 is, preferably but not necessarily, a non-captive shaft, linear actuator stepper motor having the leadscrew as the motor shaft 83 to move axially as it is driven by a threaded nut (not shown) which again can be formed on the inside of the rotor disposed within the housing 84 of the piston stepper motor 601. The HSI 36000 Series noted above with respect to the syringe stepper motor 501 is likewise suitable for the piston stepper motor 601.

Figure 12:
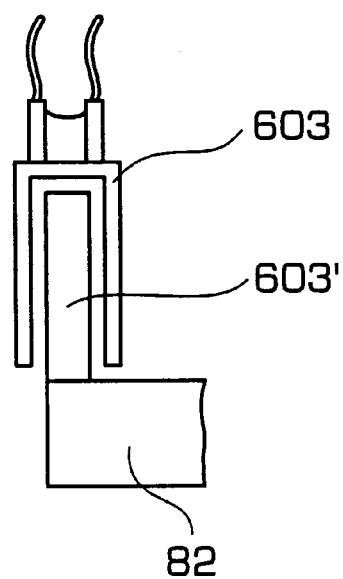
FIG. 12 is a fragmentary close-up view showing details of an optical sensor.

The piston home sensor 603 is an optical sensor having its logic output connected to the input line of the CPU 100. More specifically, the piston home sensor 603 is fixedly mounted to a side portion of the lower end of the vertical support bar 64'. As shown in FIG. 12, a plate 603' extends from a portion of the piston actuator flag 82 which, as noted above, is fixed to the piston elevator 80. Accordingly, as the piston stepper motor 601 causes the motor shaft 83 to move axially, the plate 603' either interrupts the light of the optical sensor or permits the light to reach the piston home sensor 603. Thus, when the piston elevator 80 is in the fully lowered or home position, light is obscured from reaching the piston home sensor 603, thereby outputting the logic high signal.

Figure 7A:
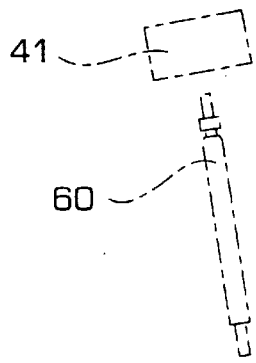
FIG. 7A is a side perspective view of the dispenser portion showing the open and closed positions of the connector house and associated elements.

As shown in FIGS. 6 and 7A, the fibrin syringe piston 70 and the pH 10 syringe piston 71 are respectively mounted on cantilever beams 610, 611 which project outwardly from a front face of the piston elevator 80. The cantilever beams 610, 611 preferably include openings (one opening 610' of which is visible in FIG. 7A) therein in order to facilitate bending thereof. The fibrin piston force sensor 602 and pH piston force sensor 602' preferably, but not necessarily, take the form of strain gauges adhered to the respective beams 610, 611. The sensors 602 and 602' are electrically connected to a printed circuit board 613 mounted to a rear surface of the piston elevator 80. The printed circuit board is in turn electrically connected through suitable wiring to the CPU 100. Accordingly, when the cantilever beams 610, 611 are deformed by the force of the pistons attempting to move upwardly within the corresponding syringes 60, 61, the resistance of the sensors 602, 602' will change.

In addition to the sensors 602 and 602' being used to evaluate the force that is demanded to move the pistons within the corresponding syringes 60, 61 in an upward or forward direction, the signal from either of the sensors 602 and 602' can also be used to detect possible blockage in the system. Blockage in the system (either fluid or other physical obstruction) can potentially lead to deformation of the bridge of the corresponding strain gauge, or loss of steps. Accordingly, the piston elevator 80 would in turn be requested to retract in case of values which are too high on the corresponding strain gauge that forms the particular sensor 602, 602'.

The sensors 602 and 602' may also be used to detect a missing piston/plunger, continue priming the syringe at a high speed and then initiate a change of speed when the fluid meets the syringe tip (as opposed to changing the speed at a given position), or indicate when the corresponding syringe piston meets the bottom or end wall of the syringe to ensure that the last drops of liquid within the syringe are dispensed therefrom. Further, the pH piston force sensor 602' may be used to detect for a low amount of pH 10.

In operation, the piston stepper motor 601 initially moves the piston elevator 80 downwardly until it reaches the piston home sensor 603. When the syringes 60, 61 have been loaded into the connector 41 and the engage command has been executed as discussed above with respect to the operation of the syringe elevator 62, the piston stepper motor. 601 will commence to move the piston elevator 80 upwardly until the 1 ml piston 71 and the 5 ml piston 70 engage into their respective syringes 61 and 60.

On the other hand, during spraying of the fibrin and the pH 10, the piston stepper motor 601 continues to move the piston elevator 80 upwardly such that the respective liquids are expelled through the spray nozzle 14, until the fibrin and pH 10 have been emptied from their respective syringes 60, 61. Once the spraying has been completed, the load/unload command will be given by pressing the load/unload button 404, and the piston stepper motor 601 will move the piston elevator 80 downwardly until it reaches the piston home sensor 603.

As shown in FIGS. 2, 3, 5, 9 and 10, the VIVOSTAT™ applicator standalone unit S is provided with the user display section 700 which displays messages for the user or operator to aid in operation of the applicator 10. The user display 700 may take the form of, for example, a vacuum fluorescent display 701 positioned at the top portion of the standalone unit S, and having a 128×16 dot matrix graphic display module which is connected to the CPU 100.

Referring to FIGS. 2, 3, 5 and 10, the user input section 400 includes a plurality of user interfaces. In particular, the pen button pressure sensor 402 comprises an air pressure sensor that has an analog output connected to an analog input channel on the CPU 100. The pen button 16 may comprise, for example, an air bladder mounted on a support 28 (see FIG. 1) and which is connected to the pen button pressure sensor 402 by the small tube 30, air tube 91 and tubing 97. Accordingly, when the user presses the pen button 16, the pressure measured by the air pressure sensor 402 rises. The CPU 100 then controls the air pump 301 and air pressure regulator 302 for providing air to the nozzle 14, and the piston stepper motor 601 in order to raise the syringe pistons based on the signal from the pen button pressure sensor 402.

Alternatively or in addition to the pen button pressure sensor 402 and pen button 16, a foot switch pressure sensor 403 (see FIGS. 3 and 5) may be provided which is a foot operated pressure sensitive switch having its analog output connected to an analog input channel on the CPU 100. Alternatively, the foot switch may take the form of an electrical contact switch. Accordingly, when the foot switch pressure sensor 403 is pressed by the operator, the output voltage decreases and the CPU 100 controls the air pump 301 and air pressure regulator 302 and the piston elevator 80 in the same manner as with the pen button pressure sensor 402.

The load/unload button 404 is a mechanical switch which is connected to a digital input line of the CPU 100. The load/unload button 404 is used to activate the opening and closing of the door 200 of the applicator 10. Thus, in order to load the applicator, the operator will press the load/unload button 404, and the door 200 will open to permit the operator to load the syringes 60, 61 and connector 41 into the applicator 10. When the syringes 60, 61 are in place, the operator will be prompted by a message in the user display section 700 to press the load/unload button 404 thereby to cause the syringe elevator 62 to lower the syringes 60, 61 and to activate closure of the door 200.

Finally, the method button 401 is a mechanical switch connected to a digital input line of the CPU 100. The method button 401 is used to select the different spraying methods. More specifically, the method button 401 may take the form of a high/low spray mode button which permits the flow rate to be varied between a high flow rate of, for example, 1.4 ml/min. and low flow rate of 0.7 ml/min. Preferably, the method button 401 is easily accessible by the user on the front of the standalone unit S together with the load/unload button 404.

Based on the method selected by the method button 401, the air supply will be set to, and maintained at, the air pressure corresponding to that method. The air supply 300 is controlled through a number of interfaces, as described in detail below.

More specifically, with reference to FIGS. 2, 3 and 5, the air pump 301 is supplied by a DC motor controlled by a transistor switch connected to a digital output on the CPU 100. An air pressure regulator 302 regulates the pressure of the air supply by releasing air through an exhaust port 302' (see FIG. 10) when the pressure is above a predetermined value set by an analog output of the CPU 100. An air pressure sensor 303 disposed within the air pressure regulator 302 is provided to sense the air pressure as it leaves the air regulator 302. The output of the air pressure sensor 303 is connected to an analog channel on the CPU 100. Further, an air flow sensor 304 is provided and senses the speed of the air as it leaves the air regulator. The output of the air flow sensor 304 is likewise connected to an analog channel on the CPU 100. As shown in FIG. 5, the air supply 300 also includes an air filter 305, a 4-way solenoid valve 306, and a moisture trap 308. The CPU 100 utilizes the pressure and flow sensor readings to control the air supply supplied by the air pump 301 to in turn send a stream of air through tubing 96, air tube 90, and the small tube 32 to the spray nozzle tip 14, where the nozzle mixes the fibrin and pH 10 with the air.

As indicated above and with reference to FIGS. 2, 3, 5, 6, 7A, 9 and 10, the door 200 is operated by the load/unload button 404. The opening and closing of the door 200 is effected by a door stepper motor 201. Preferably, but not necessarily, the door stepper motor 201 is controlled by two stepper motor drive ICs driven by four bits of an output latch on the CPU 100, with two bits for the stepper motor phase and two bits for the stepper motor current. The door stepper motor 201, preferably but not necessarily, is in the form of a captive shaft, linear actuator having a leadscrew as the motor shaft which moves axially as it is driven by an internally threaded rotor disposed within the stepper motor housing. Again, a suitable captive shaft stepper motor that may be employed is manufactured by HSI. The applicator 10 is further provided with the door open sensor 202 which is an optical sensor that detects that the door 200 is fully open, as well as a door closed sensor 203 which is likewise an optical sensor for detecting that the door 200 is fully closed.

Figure 7A:
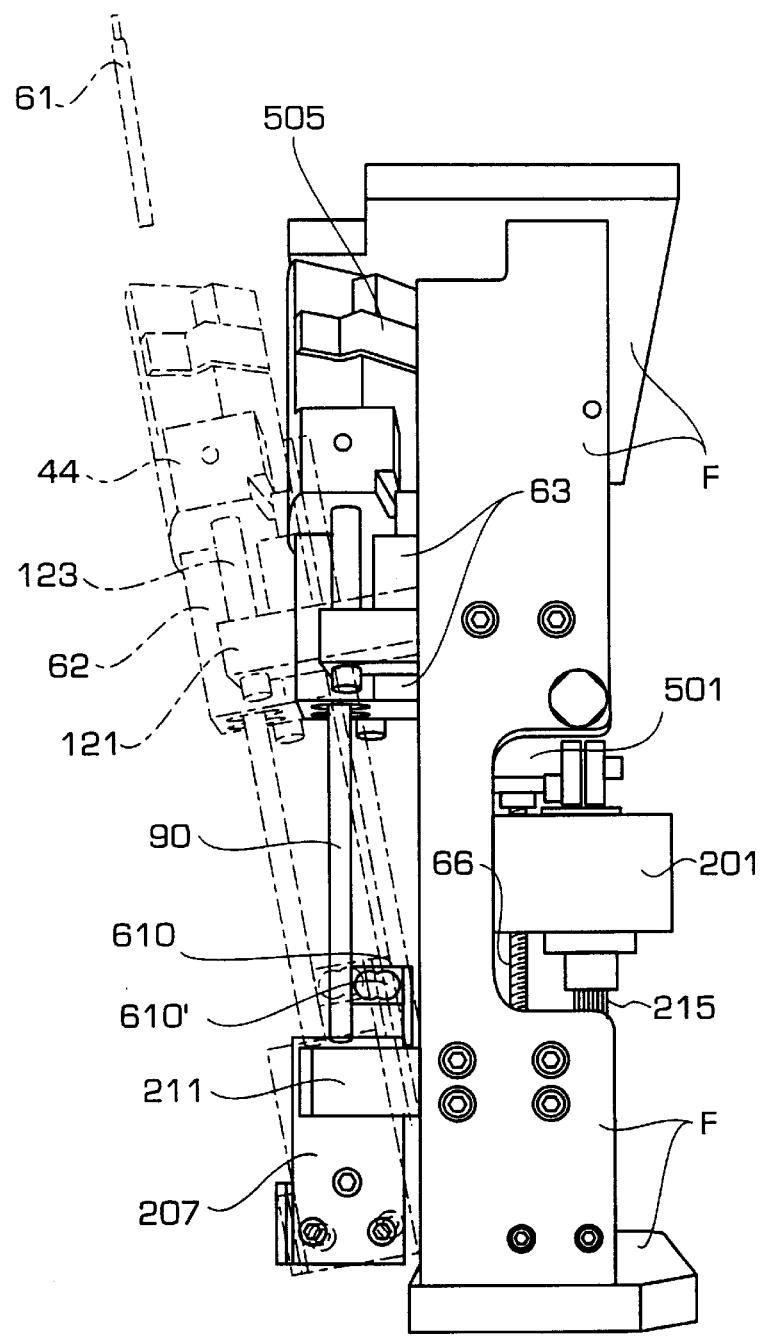
Figure 7B:
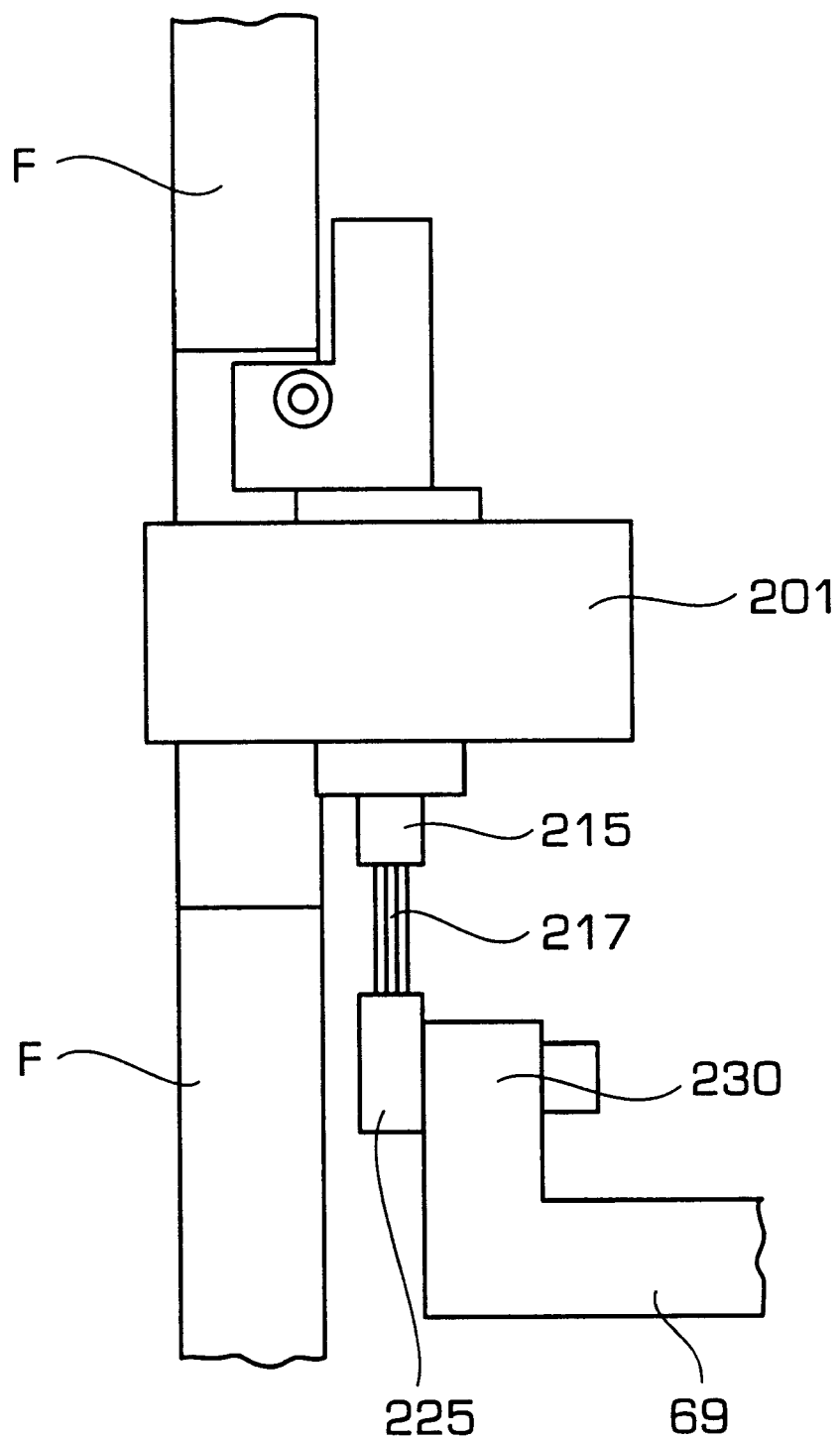
FIG. 7B is a fragmentary rear view of the door stepper motor and connection to the base member.
Figure 9:
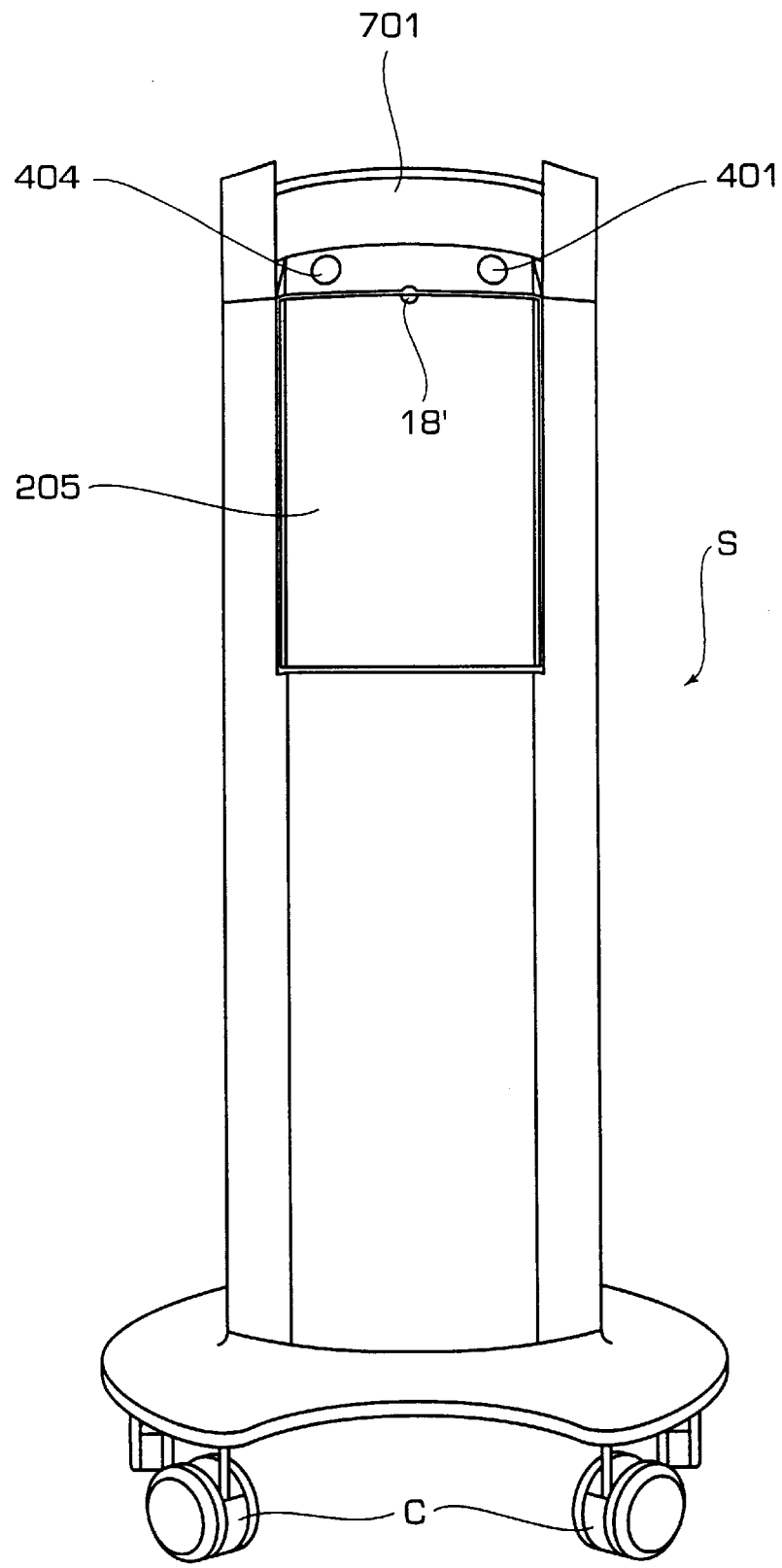
FIG. 9 is a perspective view of the standalone cabinet or housing of the applicator.
Figure 10:
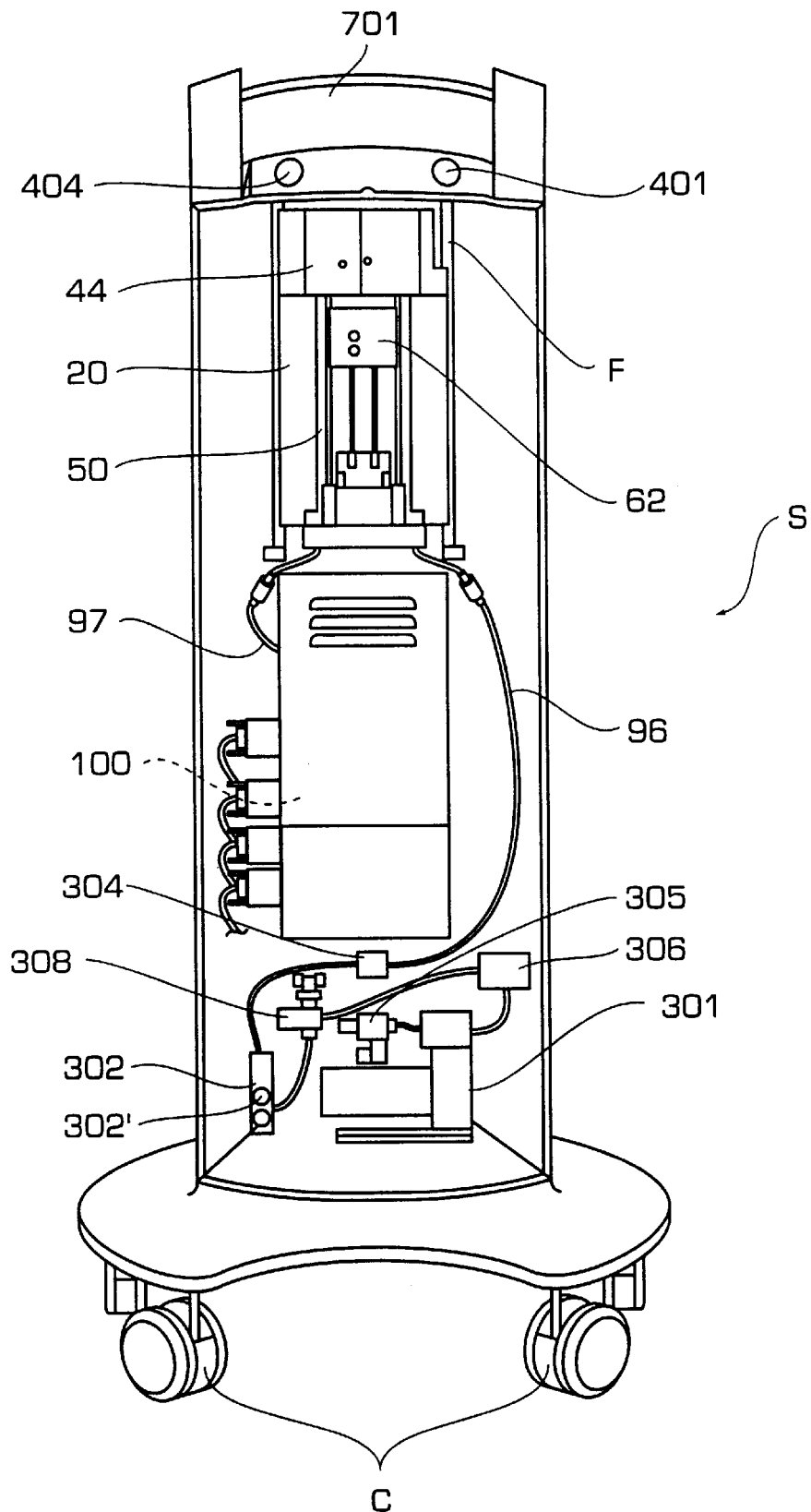
FIG. 10 is a perspective view of the standalone cabinet or housing unit similar to FIG. 9 but with a front panel of the cabinet removed to expose the inside thereof.
Figure 11:
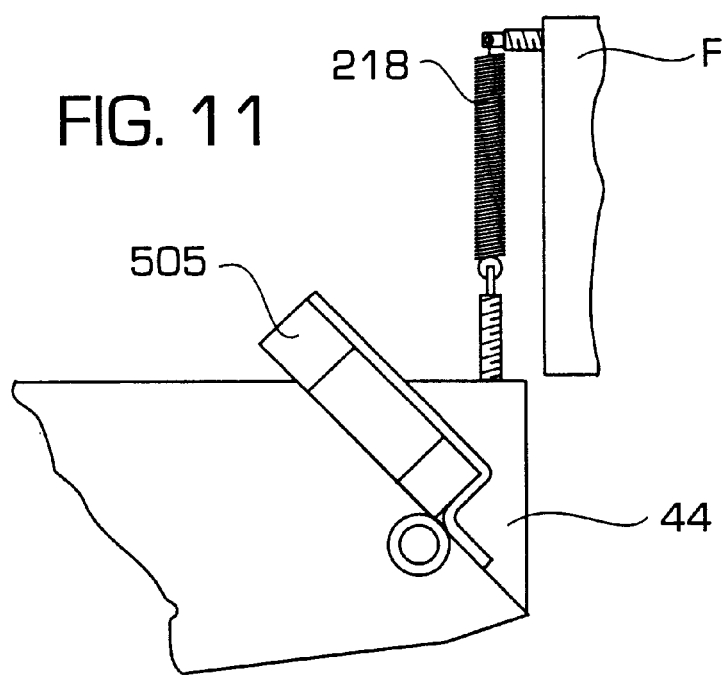
FIG. 11 is a fragmentary top view showing a tension spring.

More specifically, the door 200 comprises a door member 205 which is fixedly mounted by fasteners to the top of the connector house 44. The fasteners are fixed into threaded bores 204, 204' (see FIG. 8) formed in the top of the connector house 44. As shown in FIG. 9, the door member 205 cooperates with the cabinet of the standalone unit S to form an aesthetically pleasing exterior housing portion of the VIVOSTAT™ applicator 10. A tubing exit opening 18' is provided for permitting the tubing 18 to extend beyond the standalone unit S. The opening and closing of the door 200 will now be described with reference to the drawings. In particular, as shown in FIGS. 6 and 7, the base member 69 includes two vertically extending plates 206 and 207. The plates 206 and 207 are pivotally attached at main pivots 212, 213 to horizontally extending arms 210 and 211 which are in turn fixedly attached to the frame F. The door stepper motor 201 is fixedly mounted to a rear portion of the right side of the frame F (see FIG. 6) and includes a motor shaft 215 extending vertically downwardly from the stepper motor housing 216. As shown in FIG. 7B, the lower end 217 of the stepper motor shaft 215 is mounted in a block 225 which is in turn pivotally mounted to a vertical plate 230 extending upwardly from the right rear corner of the base member 69. A tension spring 218 (see FIG. 11) preferably is connected between the frame F and the back of the connector house 44 to remove lash and thereby smooth out the door opening/closing operation.

Accordingly, when the door stepper motor 201 is activated, the door stepper motor shaft 215 moves axially upwardly thereby causing the base member 69 to pivot with respect to the horizontal arms 210, 211 mounted to the frame F. As shown by the phantom lines in FIG. 7A, as the base member 69 pivots forwardly, the vertical support bar 64', the linear slide 64, the cross plate 68, the connector house 44, the syringe elevator 62 and related elements, the piston elevator 80 and related elements, and the air tubes 90 and 91, all together with the door member 205, pivot outwardly about the main pivots 212, 213 to expose the connector house 44 for allowing the operator to load the connector 41 with the syringes 60, 61 installed thereon into the recess 45 and respective syringe bores 46 and 47.

In order to close the door 200 and return the connector house 44 back to an operative position, the stepper motor shaft 215 moves axially downwardly so as to cause the base plate 69 to return to its original horizontally disposed position (see solid lines in FIG. 7A).

The door open sensor 202 and the door closed sensor 203, which as noted above are optical sensors, are mounted on an inside surface of the frame F at a location above the door stepper motor 201. A plate (not shown) is fixedly mounted to the upper surface of the cross plate 68 at a rear right hand corner portion thereof. The plate is operative (similar to plate 603' in FIG. 12) to interrupt the light of the respective optical door sensors 202 and 203 depending on whether the door is opened or closed.

The overall operation of the VIVOSTAT™ applicator 10 will now be described.

In particular, the operator, e.g., surgical staff, controls the VIVOSTAT™ applicator 10 by pressing the various buttons/controls including the load/unload button 404, the method button 401, the pen button 16 and/or foot switch 403, as examples. The status of the applicator 10 is reported back to the operator by prompts or messages which are displayed on the face of the applicator 10 at the user display 700. Under normal circumstances, a single operational use of the applicator 10 can be divided into four steps: loading, priming, patient spraying and unloading.

After the application of power, the VIVOSTAT™ applicator 10 preferably makes sure that the piston elevator 80 and the syringe elevator 62 are in the home position and the door 200 is closed. The applicator 10 also surveys its status and determines whether it is ready for use. In order to insure the "freshness" of the sealant, if a syringe 60, 61 or the connector 41 is detected, the door 200 will open and request that the operator remove the syringes 60, 61 and connector 41 that are present. If a serious error is detected, the error will be reported on the user display 700, and the applicator 10 will not allow the operator to continue.

In order to load the applicator, the operator presses the load/unload button 404. The door 200 will open and the operator will be prompted by a display message on the user display 700 to load the fibrin and pH 10 syringes 60, 61 and the connector 41. When the fibrin and pH 10 syringes 60, 61 are in place, the operator will be requested to press the load/unload button 404. Pressing the load/unload button 404 will cause the syringe elevator 62 to lower the syringes 60, 61 and the door stepper motor 201 to close the door 200. Once the door 200 is closed, the syringe elevator 62 and the piston elevator 80 are raised to engage the fibrin and pH 10 syringes 60, 61 with the connector 41 and to allow the spring biased air tubes 90, 91 to move up and engage with the connector 41. An air pressure test is then performed to insure both proper operation of the air supply and also to insure a good seal between the air supply and the connector 41.

Once the applicator 10 has been loaded, it is necessary to prime the air from the fibrin and pH 10 syringes 60, 61, as well as the tubing 18. A display message in the user display 700 will prompt the operator to initiate this action. The operator should point the tip or spray nozzle 14 of the applicator spray pen 11 in a safe direction and press either the pen button 16 or foot switch 403. Once either the pen button 16 or the foot switch 403 is pressed, the priming process begins. As the piston elevator 80 rises in turn causing the fibrin and pH 10 syringe pistons 60, 61 to move upwardly, the forces moving against the fibrin and pH 10 syringes 60, 61 are measured by the fibrin piston force sensor 602 and pH 10 piston force sensor 602', respectively. Within each of the fibrin and pH 10 syringes 60, 61, when all of the air has been primed, liquid enters the tubing 18 and the resistance against the piston's upward movement rises noticeably. In a normal priming operation, the pH 10 syringe 61 will be primed significantly before the fibrin syringe 60. Once the syringes have been primed, the pistons will then be raised by the piston stepper motor 601 a fixed number of steps so as to prime the tubing 18 which leads to the applicator spray pen 11.

After the priming step is complete, the applicator 10 is ready for use. Spraying of the sealant from the applicator spray pen 11 occurs either when the pen button 16 or the foot switch 403 is pressed. The particular spraying method is selected by pressing the method button 401, so as to select, for example, a high flow rate of 1.4 ml/min or a low flow rate of 0.7 ml/min. Depending upon the method selected, the air supply will be set to, and maintained at, the air pressure corresponding to that method. The air pump 301 will be turned on. Meanwhile, the piston stepper motor 601 raises the fibrin and pH 10 syringe pistons 70, 71 at a rate that corresponds to the selected method (high/low). At the start of each spray, the piston stepper motor 601 will move the pistons upward quickly for a short moment to build up pressure within the tubing 18. This will insure that the spray will have a quick, discrete start. On the other hand, when the pen button 16 or foot switch 403 is released, the piston stepper motor 601 will move the pistons downwardly quickly for a short moment to release pressure within the tubing 18. This insures that the spray will have a discrete stop. Also, the air pump 301 will be turned off after the pen button 16 or foot switch 403 is released.

To unload the VIVOSTAT™ applicator 10, the operator presses the load/unload button 404. This causes the piston stepper motor 601 to move the pistons to the home position. Then, the syringe stepper motor 501 moves the syringe elevator 62 to the home position. Finally, the door 200 to the VIVOSTAT™ applicator 10 opens and the syringes are raised for easy removal.

In addition, the applicator 10 automatically unloads when either a major system failure has occurred, or if the syringe pistons 70, 71 reach the empty position.

It is contemplated that numerous modifications may be made to the VIVOSTAT™ applicator and the applicator drive system of the present invention without departing from the spirit and scope of the invention as defined in the following claims.

What is claimed is:

1. An electro-mechanical applicator drive system for automatically emptying liquid components from a plurality of syringes, each of the syringes having a corresponding syringe piston, said applicator drive system comprising:
   a) a piston elevator section which moves the syringe pistons in unison;
   b) at least one syringe piston force sensor which senses a force required by said piston elevator section to move at least one of the syringe pistons forward and outputs a force sensor signal; and
   c) a controller which controls movement of said piston elevator section based on said force sensor signal.

2. The applicator drive system as claimed in claim 1, wherein said piston elevator section comprises:
   a support bar having a cross plate mounted thereto;
   a linear slide fixedly mounted to said support bar;
   a linear slide block slidably mounted for up and down movement on said linear slide;
   a piston elevator fixedly mounted to said linear slide block, the syringe pistons being mounted to the piston elevator;
   a piston actuator flag fixedly mounted to said piston elevator; and
   a piston stepper motor fixedly mounted to said cross plate and having an axially movable motor shaft extending downwardly and having a lower end connected to said piston actuator flag,
   whereby as said motor shaft moves axially up or down, said piston actuator flag, said linear slide block, said piston elevator and the syringe pistons all move up or down as a unit with respect to said linear slide.

3. The applicator drive system as claimed in claim 2, wherein said at least one syringe piston force sensor is mounted to said piston elevator proximate to at least one of the syringe pistons.

4. The applicator drive system as claimed in claim 3, wherein said at least one syringe piston force sensor comprises a strain gauge.

5. The applicator drive system as claimed in claim 2, wherein a pair of syringe piston force sensors is mounted to said piston elevator, with each syringe piston force sensor being located proximate to a corresponding one of the syringe pistons.

6. The applicator drive system as claimed in claim 1, further comprising a syringe elevator section which moves the syringes for loading/removal.

7. The applicator drive system as claimed in claim 6, wherein said syringe elevator section comprises:

a support bar having a cross plate mounted thereto;
a linear slide fixedly mounted to said support bar;
a monorail plate slidably mounted for up and down movement on said linear slide;
a syringe actuator flag fixedly mounted to said monorail plate;
a syringe elevator fixedly mounted to said monorail plate;
a syringe stepper motor fixedly mounted to said cross plate and having an axially movable motor shaft extending upwardly and having an upper end connected to said syringe actuator flag,
whereby as said motor shaft moves axially up or down, said syringe actuator flag, said monorail plate, and said syringe elevator all move up or down as a unit with respect to said linear slide.

8. An application system for co-applying a plurality of liquid components from a plurality of corresponding syringes, each of the syringes having a corresponding syringe piston, said application system comprising:
   a) a standalone housing unit;
   b) a dispenser disposed within said standalone housing unit and having an applicator drive system; and
   c) a disposable application set which includes a connector to which the syringes are installed and which is operative to be loaded into said dispenser, a hand-held applicator, and a tubing system for providing fluid communication between said connector and said hand-held applicator;
   wherein said applicator drive system comprises:
      i) a piston elevator section which moves the syringe pistons in unison;
      ii) at least one syringe piston force sensor which senses a force required by said piston elevator section to move at least one of the syringe pistons forward and outputs a force sensor signal; and
      iii) a controller which controls movement of said piston elevator section based on said force sensor signal.

9. The application system as claimed in claim 8, wherein said piston elevator section comprises:
   a support bar having a cross plate mounted thereto;
   a linear slide fixedly mounted to said support bar;
   a linear slide block slidably mounted for up and down movement on said linear slide;
   a piston elevator fixedly mounted to said linear slide block, the syringe pistons being mounted to the piston elevator;
   a piston actuator flag fixedly mounted to said piston elevator; and
   a piston stepper motor fixedly mounted to said cross plate and having an axially movable motor shaft extending downwardly and having a lower end connected to said piston actuator flag,
   whereby as said motor shaft moves axially up or down, said piston actuator flag, said linear slide block, said piston elevator and the syringe pistons all move up or down as a unit with respect to said linear slide.

10. The application system as claimed in claim 9, wherein said at least one syringe piston force sensor is mounted to said piston elevator proximate to at least one of the syringe pistons.

11. The application system as claimed in claim 10, wherein said at least one syringe piston force sensor comprises a strain gauge.

12. The application system as claimed in claim 9, wherein a pair of syringe piston force sensors is mounted to said piston elevator, with each syringe piston force sensor being located proximate to a corresponding one of the syringe pistons.

13. The application system as claimed in claim 8, further comprising a syringe elevator section which moves the syringes for loading/removal.

14. The application system as claimed in claim 13, wherein said syringe elevator section comprises:
   a support bar having a cross plate mounted thereto;
   a linear slide fixedly mounted to said support bar;
   a monorail plate slidably mounted for up and down movement on said linear slide;
   a syringe actuator flag fixedly mounted to said monorail plate;
   a syringe elevator fixedly mounted to said monorail plate;
   a syringe stepper motor fixedly mounted to said cross plate and having an axially movable motor shaft extending upwardly and having an upper end connected to said syringe actuator flag,
   whereby as said motor shaft moves axially up or down, said syringe actuator flag, said monorail plate, and said syringe elevator all move up or down as a unit with respect to said linear slide.

15. The application system as claimed in claim 8, wherein said standalone housing unit comprises a door member at a front portion thereof thereby to permit access to said dispenser.

16. The application system as claimed in claim 8, further comprising a door section including:
   a door member positioned at a front portion of said standalone housing unit and which is fixedly mounted to said dispenser, said dispenser being pivotally mounted within said standalone housing unit; and
   a door stepper motor for pivoting said dispenser and in turn opening/closing said door member.

17. The application system as claimed in claim 16, wherein said door section further comprises a door open sensor and a door closed sensor mounted within said standalone housing unit and connected to said controller.

18. The application system as claimed in claim 16, further comprising a load/unload button positioned at the front portion of said standalone housing unit and which activates the opening and closing of said door member, said load/unload button being connected to said controller.

19. The application system as claimed in claim 8, further comprising a method button positioned at a front portion of said standalone housing unit and which permits selection of different flow rates of the liquid components being applied from said hand-held applicator, said method button being connected to said controller.

20. The application system as claimed in claim 8, wherein said standalone housing unit is provided with a user display section which displays messages for a user to aid in operation of said application system.

21. The application system as claimed in claim 8, further comprising a gas supply section which supplies gas to said dispenser and said disposable application set, such that the plurality of liquid components are co-applied with the gas to form a spray at a spray tip of said hand-held applicator.

22. The application system as claimed in claim 21, wherein said gas supply section includes a gas pump, and wherein said hand-held applicator includes a button which activates said controller, said controller in turn controlling said gas pump.

* * * * *